United States Patent [19]

Huhn et al.

[11] 4,182,892

[45] Jan. 8, 1980

[54] MALONIC ESTERS

[75] Inventors: Magda Huhn; Eva Somfai; Gabor Szabo; Gabor Resofszki; Livia Gneth nee Zalantai, all of Budapest, Hungary

[73] Assignee: Chinoin Gyogyszer es Vegyeszeti Termekek Gyara Rt, Budapest, Hungary

[21] Appl. No.: 881,008

[22] Filed: Feb. 24, 1978

Related U.S. Application Data

[63] Continuation-in-part of Ser. No. 698,063, Jun. 21, 1976.

[30] Foreign Application Priority Data

Jun. 20, 1975 [HU] Hungary .............................. CI 1592

[51] Int. Cl.$^2$ ................. C07D 213/02; C07D 307/34; C07D 333/02
[52] U.S. Cl. ................................. 549/79; 260/347.4; 546/342; 549/65; 549/66; 549/68; 549/77
[58] Field of Search ..................... 260/332.2 A, 347.4; 546/342

[56] References Cited

U.S. PATENT DOCUMENTS 3,312,703   4/1967   Wiggins et al. ..................... 546/342

*Primary Examiner*—Alan L. Rotman
*Assistant Examiner*—Robert C. Whittenbaugh
*Attorney, Agent, or Firm*—Karl F. Ross

[57] ABSTRACT

A compound of the formula I:

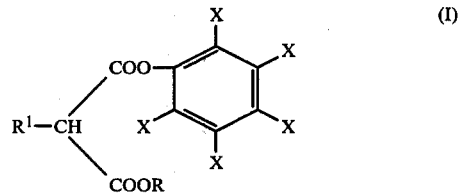

wherein:
  R is substituted or unsubstituted $C_{1-6}$ alkyl, a substituted or unsubstituted aromatic ring, a heterocyclic ring, a cycloalkyl group or a fused ring system,
  $R^1$ is hydrogen, lower alkyl, cycloaliphatic or heterocyclic ring, and
  X is a halogen atom.

6 Claims, No Drawings

MALONIC ESTERS

CROSS REFERENCE TO RELATED APPLICATION

This application is a continuation-in-part of our co-pending application Ser. No. 698,063 filed June 21, 1976 but claims only subject matter fully disclosed and claimed in said application Ser. No. 698,063 as originally filed.

Field of the Invention

The present invention relates to malonic acid esters and to a process for producing same.

DESCRIPTION OF THE INVENTION

The compounds of the present invention have the formula (I):

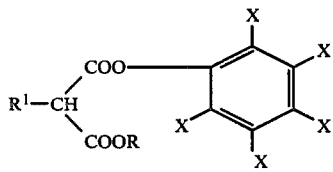

wherein
R is a substituted or unsubstituted $C_1$ to $C_6$ alkyl, a substituted or unsubstituted aromatic, heterocyclic, or cycloalkyl ring or a fused ring system;
$R^1$ is hydrogen, lower alkyl, aralkyl which can be unsubstituted or is substituted with halogen or an alkyl, a substituted or unsubstituted aromatic, cycloaliphatic or heterocyclic ring; and X is halo.

Compounds in which $R^1$ are aromatic or aralkyl have been claimed in the parent application.

Such compounds can be produced by reacting the reactive carbonic acid derivatives, preferably, halogenides of malonic acid derivatives having the formula (II):

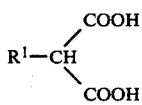

with phenol derivatives of the formula III:

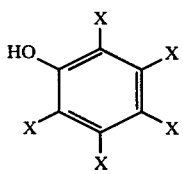

or with their salts or with compounds of the formula IV:

  HO—R    (IV)

or their salts in one or more steps.

In the formulae (II)–(IV), R and $R^1$ have the meanings stated above while $R^2$ (below) can be phenol, thienyl, furyl or pyridyl which can be unsubstituted or substituted with a radical selected from the group which consists of: halo, nitro, dialylamino, alkoxy and trifluoromethyl.

In all of the formulas given herein, X and Y can represent a halogen atom.

The present application is also concerned with the method or process and primarily with compounds in which $R^1$ or $R^2$ are thienyl, furyl or pyridyl, hydrogen or alkyl, unsubstituted or substituted to the extent indicated above.

Whenever the term "alkyl" is used herein, $C_1$ to $C_6$ alkyl is preferred, "cycloalkyl" is preferably $C_3$ to $C_8$ cycloalkyl.

Whenever an "aromatic ring" is referred to herein, the ring is preferably phenyl or naphthyl. Similarly, reference to aryl, aralkyl and terms of similar significance are intended to refer to moeities consisting of or containing the phenyl group. The "heterocyclic ring" can be a five or six membered ring having 1, 2 or 3 nitrogen, sulphur or oxygen hetero atoms. Cycloaliphatic is intended to refer to $C_3$ to $C_8$ cycloalkyl.

The "fused ring system" is preferably naphthyl.

Reference to the term "halo" herein is intended to mean the fluoro, chloro, bromo or iodo halo derivatives.

According to the inventin, halomalonic acids of the formula (V):

preferably chloro-, bromo- or iodomalonic acid, can be used as a starting material for the process of the present invention.

A starting material of the formula (II) can be prepared by methods known per se. For example, dihalomalonic acids may be prepared starting from monosubstituted malonic acids, while halomalonic esters can be prepared starting from hemiesters, with a haogenating agent. Hemiesters can have the formula (VI):

Suitable halogenating agents include: thionyl chloride, Wilsmayer reagent, phosphorous oxychloride, phosphorous pentachloride.

The resulting chloroacid is reacted with pentachlorophenol in the crude state as the solvent and the excess of the halogenating agent is distilled off. An acid-binding agent such as a weak tertiary base is used.

The chloroacid is prepared at a low temperature (below 50° C.) to avoid the formation of ketene.

When phosphorous pentachloride is used for the preparation of the chloroacid, the phosphorous oxychloride formed during the reaction is distilled off at a temperature below 50° C. in vacuo.

An analogous process is used if the chloroacid is prepared with an excess of thionyl chloride.

Preferably the pentachlorophenyl acid is produced in the presence of the aforementioned acid-binding agent. As the "weak" tertiary base, we prefer to use N,N-dimethylaniline.

The reaction is preferably carried out in an inert solvent, most advantageously a halogenated solvent selected from the group which consists of methylene chloride, dichloroethane, carbon tetrachloride, chloroform, benzene, xylene or acetonitrile.

Di- and mono-derivatives, respectively, of malonic acid are not purified before esterification according to the present invention. The reaction is preferably carried out by adding the chloroacid to the salt of the N,N-dimethylaniline, but the reverse order can also be used. There are also other salts suitable for this purpose.

When the esterification is carried out with a pentachlorophenyl salt at a temperature of 10° to 15° C., the resulting dipentachlorophenyl ester immediately precipitates. Pentachlorophenyl esters of the various hemi-esters, however, remain in solution and precipitate in a crystalline form only when the mixture is evaporated to dryness and the residue is triturated with alcohol.

The dipentachlorophenyl esters of the substituted malonic esters and the mixed esters of the various hemi-esters with pentachlorophenol are insoluble in alcohol and can easily be purified.

The hemiesters of the substituted malonic acid can be prepared according to the process described in U.S. Pat. No. 3,557,090.

According to the invention dipentachlorophenyl esters of the substituted malonic acid can be prepared starting from a compound of the formula (II), with phosphorous oxychloride and pentachlorophenol, in the presence of pyridine.

The reaction is preferably carried out in a solvent which can be acetone, acetonitrile or dichloromethane.

Mixed esters can be prepared according to the invention by reacting the free hydroxyl group of the corresponding hemiester with a pentahalophenol or with a salt thereof, in the presence of a water-entraining or water-trapping agent. A preferred water-trapping agent is dicyclohexylcarbodiamide.

According to a further feature of the invention the mixed esters are prepared in two steps. In the first step one forms the dipentahalophenyl ester by reacting a compound of the formula (II) or its halo derivatives with pentahalophenol or a salt thereof as described above. In the second step, the compound thus obtained is reaction with the compound of the formula R-OH in the presence preferably of one mole of a tertiary base.

Very valuable intermediates can be obtained, in accordance with the invention, by reacting a reactive derivative of phenylmalonic acid or phenylmalonic acid substituted with an $R^1$ group in a first step with benzyl alcohol, 5-indanol, ethanol, methanol, phenol, allyl alcohol, trichloroethanol, p-nitro-benzyl alcohol, phenacyl alcohol or p-nitro-phenaceyl alcohol, and reacting the haloacids of the thus obtained hemiesters with pentahalophenol or a salt thereof. Alternatively, the hemiesters are reacted with pentahalophenol in the presence of dicyclohexylcarbodiamide or phosphorous oxychloride. The $R^1$ group can be unsubstituted with $C_1$-$C_6$ alkoxy or with halogen.

The malonic esters according to the present invention are valuable intermediates in the production of malonic amides in the presence of tertiary bases.

These compounds can be used variously in organic chemistry in all cases in which a primary amino group is to be acylized selectively, forming a peptide bond and when a further free carboxyl group is needed in the acylating moiety of the molecule. Compounds of the present invention can thus advantageously be used in the acylation of sensitive amines, for example 6-aminopenicillanic acid, 7-desacetyl-cephalosporanic acid, e.g. by substituting them for the acylating agents described in the commonly owned application Ser. No. 598,692 filed July 24, 1975 which was copending with parent application Ser. No. 698,063 but which has since been replaced by application Ser. No. 812,735, filed July 5, 1977.

The following starting materials are preferred: 3-thienyldihalomalonic acid, 3-furyl-dihalomalonic acid, 3-methoxy-phenyldihalomalonic acid, 4-methoxy-phenyldihalomalonic acid, 3-pyridyldihalomalonic acid, o-chloro-phenyl-dihalomalonic acid, o-bromophenyl dihalomalonic acid, p-chloro-phenyl-dihalomalonic acid or n-butoxy-phenyl-dihalomalonic acid or the corresponding hemiesters.

The above compounds thus serve as the starting materials for derivatives which can be used for the acylation of the penam-ring or the cephem-ring to derive valuable medicaments.

The acylating reaction of the primary amines and hydroxyl groups presumably occurs through ketene so that the compounds are also suitable for the in situ preparation of ketenes.

The successful utilization of mono-substituted malonic acid derivatives for N- and O-acylation at low temperature in the presence of a tertiary base is indeed surprising since the pentachlorophenyl esters of the disubstituted malonic acids or of the succinic acids are able to react with primary amines only in substitution reactions at high temperature.

Hitherto similar N-acylation reactions required halomalonic acids. These compounds were highly disadvantageous; for example, the dicloromalonic acids were difficult to prepare in pure form because they were susceptible to polymerization and therefore gave rise to a number of byproducts when used as acylating agents.

The halogenates of malonic acid and its derivatives also decompose very easily and therefore cannot be stored. The compounds prepared according to the present invention are easily stored.

Whenever pentahalophenyl groups are involved in the system of the present invention the halo group may be one or more of fluoro, chloro, bromo or iodo.

The products can have the formula VII:

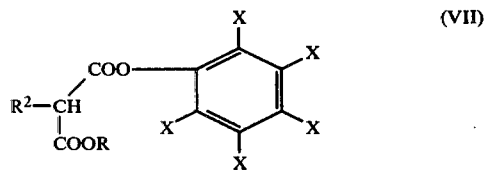

Mixed-esters, and derivatives esterified on both carboxyl-function with a pentahalophenyl group are within the scope of the present invention.

Further details of the invention are illustrated by the following Examples:

EXAMPLE 1: Dipentachloro-phenyl phenylmalonate 72 g. (0.4 mol) of phenylmalonic acid is dissolved in 600 ml. of methylene chloride, and 176 g. (0.8 mol) of phosphorous pentachloride is added. The mixture is stirred at room temperature for two hours and heated up to 50° C. to distill off methylene chloride and thereafter phosphorous oxychloride are distilled off, the latter in vacuo.

The thus-obtained residue is dissolved in 100 ml. of methylene chloride and the solution is added dropwise to a solution of 213 g. (0.8 mol) of pentachlorophenol and 80 ml. (0.8 mol) of pyridine in 800 ml. methanol, with stirring at room temperature. The precipitated white solid is stirred for 30 minutes, and thereafter is filtered. The obtained solid is washed with dry ethanol, and thus 215 g. of the named compound are obtained. Yield: 92%, melting point: 215° to 217° C.

Elemental analysis:
Calculated: C=37.7; H=0.7; Cl—54.4%;
Found: C=37.15; H=1.0; Cl=54.0%.

IR-absorptions are: 1810 (ester), 1880 (ester), 1360, 1390 (pentachlorophenyl) cm$^{-1}$.

EXAMPLE 2

The dipentachlorophenyl esters of the following malonic acid derivatives may be obtained using the procedure of the Example 1: $R^3$—CH (COO—$C_6Cl_5$)$_2$

|  |  | C% | H% | Cl% | M.p. |
|---|---|---|---|---|---|
| 3-thienyl | calc. | 33.4 |  | 52 |  |
|  | found | 33.82 |  | 51.54 |  |
| 3-furyl | calc. | 34.2 | 0.6 | 53.2 |  |
|  | found | 33.95 | 0.82 | 54.03 |  |
| 3-methoxy-phenyl | calc. | 37.4 | 1.13 | 50.0 |  |
|  | found | 37.09 | 1.0 | 49.5 |  |
| 4-methoxy-phenyl | calc. | 37.4 | 1.13 | 50.0 |  |
|  | found | 36.95 | 1.20 | 50.85 |  |
| o-chloro-phenyl | Calc. | 35.4 | 0.73 | 54.9 | 125°–128° C. |
|  | found | 36.0 | 0.93 | 54.0 |  |
| o-bromo-phenyl | calc. | 33.4 | 0.66 | 41.8 | 128°–130° C. |
|  | found | 32.9 | 0.59 | 42.3 |  |
| p-chloro-phenyl | calc. | 35.4 | 0.3 | 54.9 | 126°–128° C. |
|  | found | 36.1 | 0.95 | 54.2 |  |
| 3-pyridyl | calc. | 35.5 | 0.74 | 52.4 |  |
|  | found | 34.9 | 0.69 | 51.9 |  |

EXAMPLE 3

Following the procedure of the Examples 1 and 2 but using thionyl chloride as halogenating agent and benzene as solvent, 2 ml. of DMF is added. When the generation of hydrochloric acid is completed the benzene and the excess of thionylchloride are distilled off in vacuo, and the residue is added to the solution of the pentachlorophenol-pyridine salt in benzene. When the reaction terminates ethanol is added to the dense mixture containing precipitate to dissolve the resulted pyridine salts, and thereafter the substance is filtered off and washed with alcohol.

Products identical with the above ones are obtained. Characterizing IR absorptions for all of the products are: 1810 (ester), 1880 (ester), 1360 (pentachlorophenyl), 1390 (pentachlorophenyl) cm$^{-1}$.

EXAMPLE 4: Dipentachlorophenyl malonate 14 g. (0.1 mol) of dichloromalonic acid (Staudinger J. 41, (1908) 446) is dissolved in 50 ml. of methylene chloride, and the thus obtained solution is added to a solution of 53 g. (0.2 mol) of pentachlorophenol and 16 ml. (0.2 mol) pyridine in 300 ml. dichloromethane dropwise, at +15° C.

The precipitated solid is filtered off and washed with alcohol whereupon 42 g. of an amorphous substance (named compound) are obtained. Melting point: 195° to 197° C.

IR absorptions are: 1790 (ester), 1360 (pentachlorophenyl), 1810 (ester), 1390 (pentchlorophenyl) cm$^{-1}$.

EXAMPLE 5: Dipentachlorophenyl methylmalonate 19.4 g. (0.1 mol) of diethylmalonic acid chloride is dissolved in 70 ml. of methylene chloride. The solution is added dropwise to the solution of 53 g. (0.1 mol) of pentachlorophenol in 16 ml. (0.2 mol) of pyridine in 300 ml. of dichloromethane. The precipitated solid is filtered off, washed with alcohol, whereupon 50 g. (77%) of the named compound are obtained. Melting point: 165° to 168° C.

Elemental analysis:
Calculated: C=34.70; H=1.52; Cl=54.0%;
Found: C=34.83; H=1.48; Cl=54.39%.

IR absorptions are: 1775 (ester), 1390 (pentachlorophenyl) cm$^{-1}$.

EXAMPLE 6: Dipentachlorophenyl phenylmalonate 4.5 g. of phenylmalonic acid is suspended in 100 ml. of dichloromethne, the suspension is cooled to 0° C. and 13 g. (0.05 mol) of pentachlorophenol and 9 ml. (0.1 mol) of pyridine are added, resulting in the formation of a clear solution.

2.1 ml. of phosphorous oxychloride is added to the reaction mixture dropwise, at 0° C., the mixture is stirred for 2 hours, filtered at 0° C., and the obtained solid is washed with alcohol. Thus 7 g. of the named compound, melting at 210° to 215° C. are obtained. IR absorptions are observed at 1810 (ester), 1880 (ester), 1360, 1390 (pentachlorophenyl) cm$^{-1}$.

EXAMPLE 7: Benzyl-pentachlorophenyl phenylmalonate 32.1 g. (1.12 mol) of hemi-benzyl phenylmalonate is dissolved in 100 ml. of methylene chloride, and 22 ml. of thionyl chloride and 3 drops of DMF are added. The solution is refluxed for 2 hours. The solvent and the excess of thionylchloride is diluted with 5 ml. of dichloromethane. The thus obtained mixture is added dropwise to the solution of 31.9 g. (0.12 mol) pentachlorophenol and 9.6 ml. of pyridine, in 200 ml. dichloromethane at 10° C. The solution is stirred for 30 minutes at room temperature, the precipitated by-product is filtered off, the dichloromethane is evaporated, and the residue is triturated with dry alcohol. Filtration of the precipitated crystalline product from the cold solution yields 38.40 g. (62%) of the named compound.

Melting point=129° to 132° C.
Elemental analysis:
Calculated: C=51.16; H=2.51; 0=12.40; Cl=33.90%;
Found: C=51.43; H=2.28; 0=12.47; Cl=34.50%.

EXAMPLE 8: Ethyl-pentachlorophenyl phenylmalonate 10.40 g. (0.05 mol) of hemi-ethyl pheylmalonate is dissolved in 50 ml. of methylene chloride, and 8 ml. of thionyl chloride and one drop of dimethyl formamide are added dropwise to the solution. The mixture is stirred for 2 hours at 45° to 50° C. The solvent and the excess of the thionyl chloride are distilled off, and the chloroacid is diluted with 20 ml. of dichloromethane, and thereafter it is added to the solution of 13.30 g. (0.05 mol) of pentachlorophenol, and 4 ml. (0.05 mol) of pyridine in 80 ml. of dichloromethane. The solution is stirred at room temperature for one and a half hours. The dichloromethane is washed with 2N hydrochloric acid and water, dried and evaporated. The residue is taken up with dry alcohol, and the precipitated crystals are filtered off from the cold solution. Thus 14.40 g. (63.50%) of the named compound are obtained. Melting point=95° to 97° C.

Elemental analysis:
Calculated: C=44.93; H=2.42; O=14.09; Cl=38.50%;
Found: C=44.62; H=2.42; O=13.65; Cl=37.92%.

EXAMPLE 9: Indanyl-pentachlorophenyl phenylmalonate 14.80 g. (0.05 mol) of hemi-indanyl phenylmalonate is dissolved in 150 ml. of dichloromethane, and 8 ml. of thionyl chloride and one drop of dimethyl formamide are added dropwise. The solution is stirred at 45° to 50° C. for 2 hours. The solvent and the excess of thionyl chloride are distilled off, and the chloroacid is diluted with 30 ml. of dichloromethane and the mixture is added dropwise to the solution of 13.3 g. (0.05 mol) of pentachlorophenol and 4 ml. of pyridine in 100 ml. of dichloromethane. The solution is stirred at ambient temperature for two hours. The precipitated by-product is filtered off. The dichloromethane is shaken with 2N hydrochloric acid and water, dried, and the solvent is evaporated. The residue is triturated with dry alcohol. The precipitated crystals are filtered off from the cold solution. Thus 16.90 g. of the pure compound named above are obtained, melting at 85° to 88° C.

Elemental analysis:
Calculated: C=53.12; H=2.77; O=11.80; Cl=32.20%;
Found: C=52.94; H=2.65; O=10.95; Cl=31.80%.

EXAMPLE 10

Following the procedure described in the previous example the following hemi-pentachlorophenyl esters can be also obtained: $C_6H_5-CH(COOR^4)COOC_6Cl_5$

| $R^4$ |  | %C | %H | %Cl |
|---|---|---|---|---|
| Phenacyl | calculated | 50.73 | 2.39 | 32.00 |
|  | found | 50.21 | 2.11 | 30.08 |
| p-nitro-phenacyl | calculated | 46.90 | 2.05 | 28.90 |
|  | found | 45.92 | 1.85 | 27.80 |
| Trichloro-ethyl | calculated | 36.68 | 1.43 | 50.36 |
|  | found | 35.98 | 1.12 | 49.98 |

EXAMPLE 11: Dipentachlorophenyl malonate 5.0 g. (0.05 mol) of malonic acid is suspended in 180 ml. of acetone. 26 g. (0.1 mol) of pentachlorophenol and 9 ml. (0.1 mol) of pyridine are added to the suspension, whereupon a clear solution is obtained. The solution is cooled to 0° C., 8.4 ml. of phosphorous oxychloride is added dropwise, and the mixture is stirred at 0.° C. for one hour, and thereafter at +10° C. for one hour. The precipitated solid is filtered off, and washed with cold alcohol. Thus 14 g. of the named compound are obtained as a white amorphous powder.

Melting point = 170° C. to 172° C.
IR peaks: 1800, 1780 (ester), 1360, 1390 (pentachlorophenyl) cm$^{-1}$.
Elemental analaysis:
Calculated: C=30.1; Cl=58%;
Found: C=30.47 Cl=59.3%.

EXAMPLE 12. Dipentachlorophenyl allylmalonate 41.6 g. (0.2 mol) of phosphorous pentachloride is suspended in 200 ml. of benzene, and 14 g. (0.1 mol) of allylmlonic acid is added in small portions at +10° C. The mixture is heated to 50° C. to 60° C. till the generation of hydrogenchloride terminates, the solvent and the oxychloride are evaporated in vacuo, the chloroacid (15.9 g.) is dissolved in 50 ml. of carbon tetrachloride and it is added dropwise to the solution of 53 g. (0.2 mol) of pentachlorophenol and 16 ml. (0.2 mol) of pyridine in 500 ml. of carbon tetrachloride. The precipitated solid is filtered off and washed with carbon tetrachloride and alcohol. The thus obtained amorphous substance are dried. 46.6 g. of the named compound are obtained, melting at 155° C. to 158° C.

IR absorptions are: 1800–1780 (ester), 1340–1360 (pentachlorophenyl) cm$^{-1}$.
Elemental analysis:
Calculated: C=34.00; Cl=55.5%;
Found: C=33.85; Cl=54.95%.

EXAMPLE 13: Dipentachlorophenyl ethylmalonate 41.6 g. (0.2 mol) of phosphorous pentachloride is suspended in 150 ml. of benzene and 12.0 g. (0.1 mol) of ethylmalonic acid is added in small portions. The mixture is stirred at 50° C. for two hours, the benzene is distilled off, and the phosphorous oxychloride is dissolved in 50 ml. of carbon tetrachloride. Thereafter the resulting solution is added dropwise to a solution of 53.2 g. (0.2 mol) of pentachlorophenol and 16 ml. (0.2 mol) pyridine in 150 ml. of carbon tetrachloride. The reaction mixture is stirred at room temperature, and the solid is filtered off, suspended with alcohol on the filter, and washed with alcohol. 51.0 g. (81%) of the named compound are obtained as a white amorphous powder, melting at 148° C. to 150° C.

IR peaks: 1800 (ester), 1780 (ester) cm$^{-1}$.
Elemental analaysis:
Calculated: C=32.7; H=0.96; Cl=56.09%;
Found: C=32.1; H=0.80; Cl=55.50%.

EXAMPLE 14. Dipentachlorophenyl benzylmalonate 105 g. (0.52 mol) of phosphorous pentachloride are dissolved in 600 ml. of benzene and 50 g. (0.26 mol) of benzylmalonic acid is added. The solution is kept at 50° C. till the generation of hydrochloric acid terminates, thereafter the benzene and phosphorous oxychloride are distilled off. The residue is dissolved in 50 ml. of carbon tetrachloride and it is added dropwise to the solution of 143 g. (0.5 mol) of pentachlorophenyl and 42 ml. (0.5 mol) pyridine in 500 ml. of carbon tetrachloride. The precipitated substance is filtered off, washed with alcohol. Thus 80 g. (50%) of the named compound are obtained.

IR absorption is observed at 1800 (ester) cm$^{-1}$.
Elemental analysis:
Calculated: C=38.40; H=1.27; Cl=51.50%;
Found: C=39.00; H=1.30; Cl=50.90%.

EXAMPLE 15: Dipentachlorophenyl furylmethylmalonate 41.6 g. (0.2 mol) of phosphorous pentachloride is suspended in 150 ml. of benzene and 18 g. (0.1 mol) of furylmethyl malonic acid is added with cooling. The mixture is heated at 50° C. to 60° C., and kept at this temperature till the generation of hydrochloric acid terminates. The benzene and phosphorous oxychloride are distilled off, the remaining chloroacid is dissolved in 50 ml. of carbon tetrachloride and is added to the solution of 52.0 g. (0.2 mol) of pentachlorophenol and 18 ml. of pyridine in 200 ml. of carbon tetrachloride. The precipitated solid is filtered off, and washed with alcohol.

IR absorption is observed at 1790 (ester) cm$^{-1}$.

Elemental analysis:

Calculated: C=35.10; Cl=54.0%;
Found: C=34.90; Cl=53.50%.

EXAMPLE 16: Phenylpentachlorophenyl phenylmalonate 25 g. (0.1 mol) of hemi-phenyl phenylmalonate is suspended in 200 ml. of benzene and 20 ml. of thionyl chloride and 4 to 5 drops of dimethyl formamide are added. The mixture is stirred at 50° C. to 60° C. till solution completes. The solution is left at the previous temperature for another hour, thereafter the solvent is evaporated, the residue is taken up in 50 ml. of carbon tetrachloride, and it is added dropwise to the solution of 26.6 g. (0.1 mol) of pentachlorophenol and 8 ml. (0.1 mol) of pyridine in 300 ml. of carbon tetrachloride at 25° C. to 30° C. The precipitated pyridine chlorohydrate is washed with 2-fold 100 ml. of N hydrochloric acid, and then with 100 ml. of water. The carbon tetrachloride solution is evaporated after drying. The residue is triturated with 100 ml. of ethanol at +5° C. to +10° C., and thereafter it are filtered off. 39 g. of the named compound are obtained as a white amorphous powder. Yield: 75%, melting point: 115° C. to 118° C.

IR absorptions are: 1800 (ester), 1760 (ester) cm$^{-1}$.

Elemental analysis:

Calculated: C=49.5; H=2.17; Cl=35.00%;
Found: C=49.75; H=2.36; Cl=36.00%.

EXAMPLE 17: 2,4-Xylenyl-pentachlorophenyl phenylmalonate 10 g. (0.355 mol) of hemi-2,4-xylenyl phenylmalonate is dissolved in 50 ml. of carbon tetrachloride, and 9.3 g. (0.035 mol) of pentachlorophenol and 7.35 g. of DCC in 50 ml. of carbon tetrachloride are added dropwise. The mixture is stirred at room temperature for 3 hours and thereafter it is filtered. The solution is evaporated, and the residue is triturated with alcohol. Thus 8 g. of the named compound are obtained. Yield: 50%, melting point: 108° C. to 110° C.

Elemental analysis:

Calculated: C=52.0; H=2.83; Cl=33%;
Found: C=51.91; H=2.90; Cl=33.54%.

EXAMPLE 18: 3,4-Xylenyl-pentachlorophenyl phenylmalonate 8.5 g. (0.03 mol) of hemi-3,4-xylenyl phenylmalonate is suspended in 100 ml. of benzene, 4 to 5 drops of dimethyl formamide and 3.2 ml. (0.045 mol) of thionylchloride are added. The mixture is stirred for two hours at 45° C. to 50° C., and the thionyl chloride and benzene are distilled off under a nitrogen atmosphere. The residue is diluted with 50 ml. of carbon tetrachloride and it is added dropwise to the solution of 7.98 g. (0.03 mol) pentachlorophenol and 2.4 ml. (0.03 mol) of pyridine in 100 ml. of carbon tetrachloride. The precipitated pyridine chlorohydrate is washed with 50 ml. of 2N hydrochloric acid. The solution is evaporated, and the residue is triturated with cold alcohol. Thus 10 g. (67%) of the named compound are obtained, melting at 125° C. to 128° C.

IR absorptions are: 1800 (pentachlorophenyl), 1760 (3,4-xylenyl)cm$^{-1}$.

Elemental analysis:

Calculated: C=51.00; H=2.83; Cl=33%;
Found: C=51.09; H=2.40; Cl=34.54%.

EXAMPLE 19: Indanyl-pentachlorophenyl phenylmalonate 23.68 g. (0.08 mol) of hemi-indanyl phenylmalonic acid is dissolved in 200 ml. of benzene, 8.8 ml. (0.12 mol) of thionylchloride and 6 to 8 drops of dimethyl formamide are added, and the mixture is stirred at 45° C. to 50° C. for two hours till the generation of hydrochloric acid gases terminates. Benzene and the excess of thionyl chloride are distilled off in high vacuo. The residue is dissolved in 50 ml. of carbon tetrachloride and the thus obtained solution is added dropwise to the solution of 21.28 g. (0.08 mol) pentachlorophenol and 150 ml. of carbon tetrachloride in 6.4 ml. (0.08 mol) of pyridine. The solution is stirred for one hour at room temperature. Thereafter it is decomposed with 100 ml. of 2N hydrochloric acid, and it is washed with 3×50 ml. of 2N hydrochloric acid and 1×150 ml. of sodiumchloride solution. Carbon tetrachloride is added and the solvent is evaporated, and the residue is taken up with 80 ml. of absolute alcohol. When cooling the mixture, the hemiester precipitates, it is filtered off and washed with a small amount of cold alcohol. Thus 32.5 g. (75%) of the named compound are obtained, melting at 118° C. to 120° C.

IR absorptions are: 1790 (pentachlorophenyl ester), 1760 (indanyl ester) cm$^{-1}$.

Elemental analysis:

Calculated: C=53.1; H=2.77; Cl=32.2%;
Found: C=53.45; H=2.60; Cl=33.07%.

EXAMPLE 20: Indanyl-pentachlorophenyl phenylmalonate 11 g. (0.035 mol) of hemi-indanyl phenylmalonate is dissolved in 50 ml. of carbon tetrachloride and the solution of 9.3 g. (0.03 mol) of pentachlorophenol and 7.35 g. of DCC (dicyclohexylcarbodiamide) in 50 ml. of carbon tetrachloride is added dropwise. The solution is stirred for two hours at room temperature and the precipitated DCU (dicyclohexylurea) is filtered off. The carbon-tetrachloride solution is evaporated in vacuo and the residue is triturated with cold alcohol and filtered off. After drying 14 g. (74%) of the named compound are obtained, melting at 118° C. to 120° C.

IR absorptions are: 1790 (pentachlorophenyl ester), 1760 (indanyl ester) cm$^{-1}$.

EXAMPLE 21: β-naphthyl-pentachlorophenyl phenylmalonate 9 g. (0.03 mol) of hemi-naphthyl phenylmalonte is dissolved in 50 ml. of carbon tetrachloride and the solution of 7.85 g. (0.03 mol) pentachlorophenol and 6.4 g. (0.03 mol) of DCC in 50 ml. of carbon tetrachloride is added dropwise, with stirring at room temperature. The mixture is stirred for two hours, the precipitated DCU is filtered off, nd the carbon-tetrachloride solution is evaporated, the residue is triturated with alcohol, and thus 12 g. (70%) of the named compound are obtained, melting at 136° C. to 137° C.

IR absorptions are: 1800 (pentachlorophenyl ester), 1760 (β-naphthyl ester) cm$^{-1}$.

EXAMPLE 22: Phenacyl-pentachlorophenyl phenylmalonate 9 g. (0.03 mol) of hemi-phenacyl phenylmalonte is dissolved in 50 ml. of carbon tetrachloride, and the solution of 7.85 (0.03 mol) of pentachlorophenol and 6.4 g. (0.03 mol) DCC in 50 ml. of carbon tetrachloride are added dropwise, with stirring at room temperature. The mixture is stirred for two hours, the resulting DCU is filtered off, and the carbon-tetrachloride solution is evaporated. The residue is triturated with alcohol. Thus 12 g. (70%) of the title compound are obtained.

IR absorption is observed at: 1790 (pentachlorophenyl ester) cm$^{-1}$.

Elemental analysis:
Calculated: C=50.73; H=2.39; Cl=32.20%;
C=50.21; H=2.11; Cl=30.08%.

EXAMPLE 23

The following pentachlorophenyl phenylmalonate compounds may be prepared from the corresponding hemiphenylmalonates using the procedure of the previous example:

| R' |  | %C | %H | %Cl |
|---|---|---|---|---|
| p-nitro-phenacyl | calculated | 46.90 | 2.05 | 28.90 |
|  | found | 45.92 | 1.85 | 27.80 |
| trichloro-ethyl | calculated | 36.68 | 1.43 | 50.36 |
|  | found | 35.98 | 1.12 | 49.98. |

Additional compounds contemplated by the invention include:
pentachlorophenyl-cyclohexyl phenylmalonte;
pentachlorophenyl-5-indanyl phenylmalonate;
pentachlorophenyl-(acetoxy)-methyl phenylmalonate; and
pentachlorophenyl-(2,2,2-trichloro-ethyl) phenylmalonate.

We claim:

1. A compound of the formula

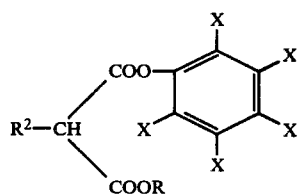

wherein
R is $C_1$ to $C_6$ alkyl, $C_1$ to $C_6$ haloalkyl, $C_3$ to $C_8$ cycloalkyl, phenyl, halophenyl, naphthyl, benzyl, indanyl, phenacyl, p-nitrophenacyl, xylyl or acetoxymethyl;
$R^2$ is thienyl, furyl, furylmethyl or pyridyl unsubstituted or substituted by halo, nitro, dialkylamino, alkoxy or trifluoromethyl; and
X is halo.

2. A compound selected from the group which consists of:
dipentachlorophenyl-3-thienyl-malonate;
dipentachlorophenyl-3-furyl-malonate;
dipentachlorophenyl-3-pyridyl-malonate; and
dipentachlorophenyl-furylmethyl-malonate.

3. A compound of the formula:

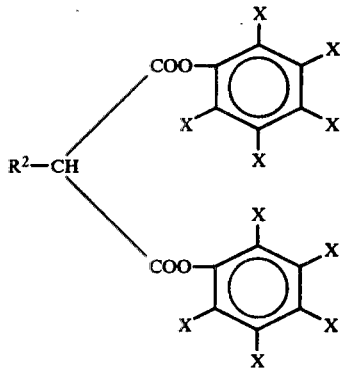

wherein
$R^2$ is thienyl, furyl, furylmethyl or pyridyl unsubstituted or substituted by halo, nitro, dialkylamino, alkoxy, or trifluoromethyl; and
X is halo.

4. A compound of the formula:

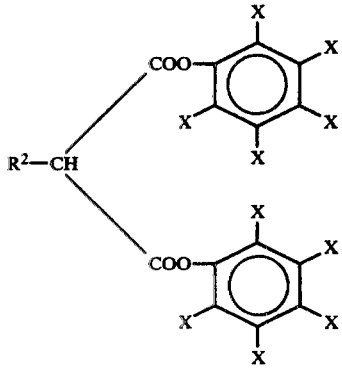

wherein
$R^2$ is thienyl, furyl, furylmethyl or pyridyl; and
X is halo.

5. A compound as defined in claim 1 wherein $R^2$ is thienyl.

6. The compound as defined in claim 5 which is dipentachlorophenyl-3-thienyl-malonate.